(12) United States Patent
Burkholz (10) Patent No.: US 9,028,425 B2
(45) Date of Patent: May 12, 2015

(54) VENTED BLOOD SAMPLING DEVICE

(75) Inventor: Jonathan Karl Burkholz, Salt Lake City, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 287 days.

(21) Appl. No.: 13/171,208

(22) Filed: Jun. 28, 2011

(65) Prior Publication Data

US 2012/0016266 A1    Jan. 19, 2012

Related U.S. Application Data

(60) Provisional application No. 61/364,455, filed on Jul. 15, 2010.

(51) Int. Cl.
| | | |
|---|---|---|
| *A61B 5/15* | (2006.01) | |
| *A61B 5/153* | (2006.01) | |
| *A61M 39/00* | (2006.01) | |

(52) U.S. Cl.
CPC ............. *A61B 5/1405* (2013.01); *A61B 5/15* (2013.01); *A61B 5/153* (2013.01); *A61M 2039/0036* (2013.01); *A61M 2205/7536* (2013.01)

(58) Field of Classification Search
CPC ......... A61B 5/1405; A61B 5/15; A61B 5/153
USPC ................. 600/573–584; 604/167.01–167.04
See application file for complete search history.

(56) References Cited

U.S. PATENT DOCUMENTS

| | | |
|---|---|---|
| 4,003,403 A | 1/1977 | Nehring |
| 4,193,399 A | 3/1980 | Robinson |
| 4,269,186 A | 5/1981 | Loveless et al. |
| 4,387,879 A | 6/1983 | Tauschinski |
| 4,444,203 A * | 4/1984 | Engelman ............... 600/577 |
| 4,449,693 A | 5/1984 | Gereg |
| 4,682,980 A | 7/1987 | Suzuki |
| 4,703,762 A | 11/1987 | Rathbone et al. |

(Continued)

FOREIGN PATENT DOCUMENTS

| | | |
|---|---|---|
| CA | 2133053 A1 | 3/1995 |
| CN | 101610809 A | 12/2009 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Sean Dougherty
*Assistant Examiner* — Michael C Stout
(74) *Attorney, Agent, or Firm* — Jeanne Lukasavage; Craig Metcalf; Kirton McConkie (57) ABSTRACT

An extravascular system is disclosed. The system includes a body, a septum, a septum activator, and a blood sampling device. The body has and inner lumen extending therethrough. The septum is disposed within the inner lumen. The septum activator is disposed within the inner lumen proximal the septum. The septum activator has an inner passage extending therethrough. The blood sampling device has a tube that is longer than a length of the septum activator and has a width less than or equal to a width of the inner passage of the septum activator. An interior of the tube is in fluid communication with a reservoir within the blood sampling device. A vent is in fluid communication with the reservoir. The vent passes air but not blood therethrough.

15 Claims, 7 Drawing Sheets

(56) References Cited

U.S. PATENT DOCUMENTS

| | | | | |
|---|---|---|---|---|
| 4,758,225 A | | 7/1988 | Cox et al. | |
| 4,765,588 A | | 8/1988 | Atkinson | |
| 4,842,591 A | | 6/1989 | Luther | |
| 4,874,377 A | | 10/1989 | Newgard et al. | |
| 4,894,052 A | | 1/1990 | Crawford | |
| 4,917,668 A | | 4/1990 | Haindl | |
| 4,917,671 A | | 4/1990 | Chang | |
| 4,935,010 A | * | 6/1990 | Cox et al. | 604/122 |
| 4,973,313 A | * | 11/1990 | Katsaros et al. | 604/165.02 |
| 5,032,116 A | | 7/1991 | Peterson et al. | |
| 5,041,097 A | | 8/1991 | Johnson | |
| 5,053,014 A | | 10/1991 | Van Heugten | |
| 5,062,836 A | | 11/1991 | Wendell | |
| 5,064,416 A | | 11/1991 | Newgard et al. | |
| 5,084,023 A | | 1/1992 | Lemieux | |
| 5,085,645 A | | 2/1992 | Purdy et al. | |
| 5,108,374 A | | 4/1992 | Lemieux | |
| 5,127,905 A | | 7/1992 | Lemieux | |
| 5,154,703 A | | 10/1992 | Bonaldo | |
| 5,156,596 A | * | 10/1992 | Balbierz et al. | 604/164.11 |
| 5,226,883 A | | 7/1993 | Katsaros et al. | |
| 5,234,410 A | | 8/1993 | Graham et al. | |
| 5,242,411 A | | 9/1993 | Yamamoto et al. | |
| 5,251,873 A | | 10/1993 | Atkinson et al. | |
| 5,269,317 A | | 12/1993 | Bennett | |
| 5,295,657 A | | 3/1994 | Atkinson | |
| 5,295,658 A | | 3/1994 | Atkinson et al. | |
| 5,295,969 A | | 3/1994 | Fischell et al. | |
| 5,295,970 A | | 3/1994 | Clinton et al. | |
| 5,330,435 A | | 7/1994 | Vaillancourt | |
| 5,338,313 A | | 8/1994 | Mollenauer et al. | |
| 5,342,316 A | | 8/1994 | Wallace | |
| 5,350,363 A | | 9/1994 | Goode et al. | |
| 5,352,205 A | | 10/1994 | Dales et al. | |
| 5,405,323 A | | 4/1995 | Rogers et al. | |
| 5,417,664 A | | 5/1995 | Felix et al. | |
| 5,441,487 A | | 8/1995 | Vedder | |
| 5,456,675 A | | 10/1995 | Wolbring et al. | |
| 5,474,544 A | | 12/1995 | Lynn | |
| 5,487,728 A | | 1/1996 | Vaillancourt | |
| 5,501,426 A | | 3/1996 | Atkinson et al. | |
| 5,501,671 A | | 3/1996 | Rosen et al. | |
| 5,520,666 A | | 5/1996 | Choudhury et al. | |
| 5,533,708 A | | 7/1996 | Atkinson et al. | |
| 5,542,932 A | | 8/1996 | Daugherty | |
| 5,549,566 A | | 8/1996 | Elias et al. | |
| 5,549,577 A | | 8/1996 | Siegel et al. | |
| 5,549,651 A | | 8/1996 | Lynn | |
| 5,575,769 A | | 11/1996 | Vaillancourt | |
| 5,613,663 A | | 3/1997 | Schmidt et al. | |
| 5,651,772 A | | 7/1997 | Arnett | |
| 5,657,963 A | | 8/1997 | Hinchliffe et al. | |
| 5,697,915 A | | 12/1997 | Lynn | |
| 5,730,123 A | | 3/1998 | Lorenzen et al. | |
| 5,738,144 A | | 4/1998 | Rogers | |
| 5,738,664 A | | 4/1998 | Erskine et al. | |
| 5,749,861 A | | 5/1998 | Guala et al. | |
| 5,806,831 A | | 9/1998 | Paradis | |
| 5,817,069 A | | 10/1998 | Arnett | |
| 5,911,710 A | | 6/1999 | Barry et al. | |
| 5,919,160 A | | 7/1999 | Sanfilippo, II | |
| 5,954,657 A | | 9/1999 | Rados | |
| 5,954,698 A | | 9/1999 | Pike | |
| 5,957,898 A | | 9/1999 | Jepson et al. | |
| 5,967,490 A | | 10/1999 | Pike | |
| 6,039,302 A | | 3/2000 | Cote, Sr. et al. | |
| 6,077,244 A | | 6/2000 | Botich et al. | |
| 6,117,108 A | | 9/2000 | Woehr et al. | |
| 6,139,534 A | | 10/2000 | Niedospial, Jr. et al. | |
| 6,171,287 B1 | | 1/2001 | Lynn et al. | |
| 6,261,282 B1 | | 7/2001 | Jepson et al. | |
| 6,273,869 B1 | | 8/2001 | Vaillancourt | |
| 6,344,033 B1 | | 2/2002 | Jepson et al. | |
| 6,485,473 B1 | | 11/2002 | Lynn | |
| 6,503,225 B1 | | 1/2003 | Kirsch et al. | |
| 6,575,960 B2 | | 6/2003 | Becker et al. | |
| 6,595,964 B2 | | 7/2003 | Finley et al. | |
| 6,595,981 B2 | | 7/2003 | Huet | |
| 6,607,513 B1 | | 8/2003 | Down et al. | |
| 6,651,956 B2 | | 11/2003 | Miller | |
| 6,669,681 B2 | | 12/2003 | Jepson et al. | |
| 6,699,221 B2 | | 3/2004 | Vaillancourt | |
| 6,740,063 B2 | | 5/2004 | Lynn | |
| 6,866,656 B2 | | 3/2005 | Tingey et al. | |
| 6,883,778 B1 | | 4/2005 | Newton et al. | |
| 6,908,459 B2 | | 6/2005 | Harding et al. | |
| 7,008,404 B2 | | 3/2006 | Nakajima | |
| 7,347,839 B2 | | 3/2008 | Hiejima | |
| 7,396,346 B2 | | 7/2008 | Nakajima | |
| 7,470,254 B2 | * | 12/2008 | Basta et al. | 604/167.04 |
| 7,736,339 B2 | | 6/2010 | Woehr et al. | |
| 7,914,494 B2 | * | 3/2011 | Hiejima | 604/167.04 |
| 2001/0014787 A1 | * | 8/2001 | Toyokawa et al. | 604/167.01 |
| 2002/0193752 A1 | | 12/2002 | Lynn | |
| 2005/0027256 A1 | | 2/2005 | Barker et al. | |
| 2005/0075606 A1 | * | 4/2005 | Botich et al. | 604/110 |
| 2005/0077225 A1 | | 4/2005 | Usher et al. | |
| 2005/0256457 A1 | | 11/2005 | Rome | |
| 2005/0256500 A1 | | 11/2005 | Fujii | |
| 2005/0273019 A1 | | 12/2005 | Conway et al. | |
| 2006/0129064 A1 | * | 6/2006 | Conway et al. | 600/576 |
| 2007/0083162 A1 | | 4/2007 | O'Reagan et al. | |
| 2007/0100284 A1 | * | 5/2007 | Leinsing et al. | 604/164.01 |
| 2007/0179456 A1 | * | 8/2007 | Glenn | 604/288.01 |
| 2008/0027389 A1 | * | 1/2008 | Hiejima | 604/167.04 |
| 2008/0039796 A1 | | 2/2008 | Nakajima | |
| 2008/0097330 A1 | * | 4/2008 | King et al. | 604/164.02 |
| 2008/0097407 A1 | | 4/2008 | Plishka | |
| 2008/0103487 A1 | | 5/2008 | Miyasaka | |
| 2008/0108944 A1 | * | 5/2008 | Woehr et al. | 604/164.08 |
| 2008/0108956 A1 | * | 5/2008 | Lynn et al. | 604/256 |
| 2008/0200904 A1 | | 8/2008 | Cluff et al. | |
| 2008/0287906 A1 | * | 11/2008 | Burkholz et al. | 604/500 |
| 2010/0204648 A1 | * | 8/2010 | Stout et al. | 604/122 |
| 2010/0204675 A1 | * | 8/2010 | Woehr et al. | 604/500 |
| 2012/0016307 A1 | * | 1/2012 | Burkholz et al. | 604/168.01 |

FOREIGN PATENT DOCUMENTS

| EP | 0 102 070 A2 | 3/1984 |
|---|---|---|
| WO | WO 99/34849 | 7/1999 |
| WO | WO 2004/098685 A1 | 11/2004 |
| WO | WO 2006/088501 | 8/2006 |

* cited by examiner

VENTED BLOOD SAMPLING DEVICE

RELATED APPLICATIONS

This application claims the benefit of U.S. Provisional Application No. 61/364,455 filed Jul. 15, 2010, entitled BLOOD CONTROL VALVE WITH VENTED BLOOD SAMPLING DEVICE IN A CLOSED IV CATHETER SYSTEM OR ANY FEMALE LUER CONNECTOR, and is incorporated herein by reference.

BACKGROUND

The present disclosure relates to the processes of venting air and blood sampling with vascular access devices. Blood sampling is a common health care procedure involving the withdrawal of at least a sample of blood from a patient. Blood samples are commonly taken from hospitalized, homecare, and emergency room patients either by finger stick, heel stick, or venipuncture. Once collected, blood samples are analyzed via one or more blood test levels.

Blood tests determine the physiological and biochemical states of the patient, such as disease, mineral content, drug effectiveness, and organ function. Blood tests may be performed in a laboratory, a distance away from the location of the patient, or performed at the point of care, near the location of the patient. One example of point of care blood testing is the routine testing of a patient's blood glucose levels, which involves the extraction of blood via a finger stick and the mechanical collection of blood into a diagnostic cartridge. Thereafter the diagnostic cartridge analyzes the blood sample and provides the clinician a reading of the patient's blood glucose level. Other devices are available which analyze blood gas electrolyte levels, lithium levels, and ionized calcium levels. Furthermore, some point-of-care devices identify markers for acute coronary syndrome (ACS) and deep vein thrombosis/pulmonary embolism (DVT/PE).

Despite the rapid advancement in point of care testing and diagnostics, blood sampling techniques have remained relatively unchanged. Blood samples are frequently drawn using hypodermic needles, or vacuum tubes coupled to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Furthermore, each required device adds time and cost to the testing process. Accordingly, there is a need for more efficient blood sampling and testing devices and methods.

SUMMARY

The present invention has been developed in response to problems and needs in the art that have not yet been fully resolved by currently available vascular access systems and methods. Thus, these systems and methods are developed to provide a blood sampling device that can vent air from an extravascular system and simultaneously collecting a sample of blood. In some embodiments, a blood sampling device replaces prior devices and procedures that took more time, used more parts, and cost more than the present blood sampling device.

In one aspect of the invention, an extravascular system comprises: a body having and inner lumen extending therethrough; a septum disposed within the inner lumen; a septum activator disposed within the inner lumen proximal the septum, the septum activator having an inner passage extending therethrough; and a blood sampling device having a tube that is longer than a length of the septum activator and having a width less than or equal to a width of the inner passage of the septum activator, an interior of the tube being in fluid communication with a reservoir within the blood sampling device, a vent in fluid communication with the reservoir, the vent passing air but not blood therethrough.

Implementation may include one or more of the following features. The tube of the blood sampling device may selectively extend through the inner passage of the septum activator and through a slit in the septum, the blood sampling device may be selectively coupled to the body. The septum may divide and substantially seal a distal chamber of the inner lumen from a proximal chamber of the inner lumen, and the septum may have one or more slits therein, the septum activator being movable from a un-activated position in the proximal chamber to an activated position that extends through the slit of the septum into the distal chamber. The blood sampling device may have a portion of an outer geometry approximately equal to that of the inner lumen of the body such that the blood sampling device can be press fit within the inner lumen of the body. The blood sampling device may have a Luer connector that selectively interlocks with a Luer connector disposed on the body. The body may be either a catheter assembly or a Luer access port. The septum and the body may form a fluid tight connection that circumscribes the septum. The reservoir may have a volume equal to or greater than about 0.1 mL. The tube may have a length greater than or equal to about 5 mm and a width of less than or equal to about 3 mm. At least a portion of the blood sampling device defining the reservoir may be compressible and may decrease the internal volume of the reservoir when compressed.

In another aspect of the invention, a blood sampling device comprises: a body defining a reservoir therein; a tube extending from the body a distance greater than the length of a septum activator of a blood control valve, the tube having a width less than the inner width of passage within a blood control valve, the interior of the tube being in fluid communication with the reservoir; and a vent coupled to the body and forming a barrier surface of the reservoir, the vent passing air but not blood therethrough.

Implementation may include one or more of the following features. The reservoir may have a volume equal to or greater than about 0.1 mL. The vent may be air permeable and hydrophobic. At least a portion of the body defining the reservoir may be compressible and may decrease the internal volume of the reservoir when compressed. The tube may have a length greater than or equal to 5 mm.

In another aspect of the invention, an extravascular system comprises: a body having and inner lumen; a septum disposed within the inner lumen; a septum activator disposed within the inner lumen proximal the septum, the septum activator having an inner passage extending therethrough; and a blood sampling device disposed at least partially within the inner lumen of the body, the blood sampling device having a tube that extends through the inner passage of the septum activator and through an opening in the septum, the blood sampling device having a reservoir therein in fluid communication with the tube and a vent in fluid communication with the reservoir, the vent passing air but not blood therethrough.

Implementation may include one or more of the following features. The septum may divide and substantially seal a distal chamber of the inner lumen from and a proximal chamber of the inner lumen, the septum may have one or more slits therein, the septum activator may be movable from a unactivated position in the proximal chamber to an activated position that extends through the slit of the septum into the distal chamber. A removable seal may be disposed across the vent preventing air from passing through the vent. The blood sampling device may be removably coupled to the body. The septum and the body may form a fluid tight connection that circumscribes the septum.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
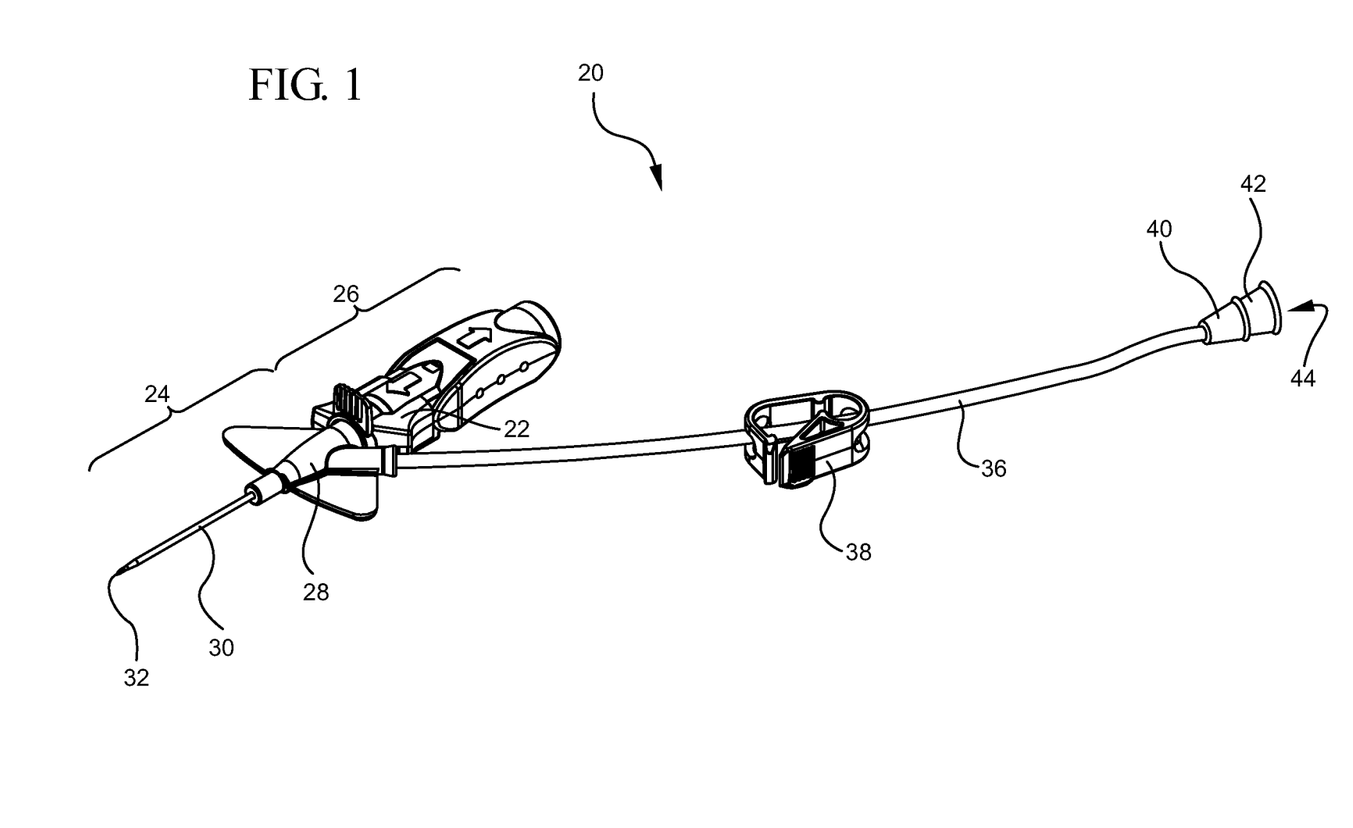
FIG. 1 is a perspective view of an extravascular system comprising a catheter assembly, intravenous tubing with a clamp, a port, and a vented blood sampling device, according to some embodiments.

Reference will now be made to FIG. 1, which illustrates an extravascular system 20 with which a blood sampling device 42 may be used. It will be understood that the blood sampling device 42 is not limited to use within these illustrated extravascular system, but may be used with other extravascular systems, ranging from a simple needle, to more complex extravascular devices. The blood sampling device 42 can, in some configurations, reduce the number of components required to draw a diagnostic blood sample from a patient. This is because the blood sampling device 42 combines the ability to perform the processes of venting the extravascular system 20 and collecting blood into a single device. Additionally, in some instance, the blood sampling device 42 and the port 40 can remove the need for the clamp 38, as described below.

FIG. 1 illustrates an extravascular system 20, such as the BD NEXIVA™ Closed Intravenous (IV) Catheter System, by Becton, Dickinson and Company, which can be accessed by a blood sampling device 42. The illustrated embodiment of the system 20 includes multiple vascular access devices such as a needle hub 26 coupled to an introducer needle 32 that extends through a catheter assembly 24. The catheter assembly 24 includes a catheter adapter 28 that is coupled to an over-the-needle, peripheral, IV catheter 30 extending therefrom. The introducer needle 32 is left within the catheter assembly 24 until the catheter 30 is inserted into and correctly positioning within the vasculature of a patient, when it is withdrawn. In some embodiments, one or more needle tip shields 22 are incorporated into the needle hub 26 to shield the tip of the introducer needle 32 after it is removed from the catheter assembly 24.

In some configurations, an integrated extension tubing 36 is coupled to and provides fluid communication with the catheter assembly 24. The extension tubing 36 can also be coupled to a port 40 that provides access to the vascular system of the patient via the extension tubing 36 and the catheter assembly 24. The port 40 can have various configurations, such as a single port Luer adapter, a Y Luer adapter, and other known ports. In some instances, a clamp 38 is used to selectively close the extension tubing 36 to prevent flow therethrough. As shown, a blood sampling device 42 can be inserted into the port 40.

While FIG. 1 depicts the blood sampling device 42 coupled to a port 40 on an extension tubing 36, the blood sampling device 42 can be coupled to any port 40 in fluid connection to the vasculature of a patient. Such alternative ports could be located on the catheter assembly 24 directly, or more specifically on the catheter adapter 28. In other extravascular system 20, ports 40 can be coupled to an introducer needle 32, catheter 30, or other components of the extravascular system 20.

In some embodiments, the blood sampling device 42 vents air from the catheter assembly 24 and the extension tubing 36 prior to collect a blood sample therefrom. When the catheter assembly 24 establishes fluid communication with the vasculature of a patient, the internal blood pressure of the vascular system can force blood into the catheter assembly 24 and up into the extension tubing 36. In some instances, it is desirable to permit this blood to fill the catheter assembly 24 and the extension tubing 36 in order to vent air from the extravascular system 20 before fluids are infused through this system into the patient. This process can reduce the likelihood that air is infused into the patient's vasculature.

Accordingly, in some embodiments, the blood sampling device 42 includes a vent 44 that is air permeable, through which air from within the extravascular system 20 passes. In some embodiments, the vent 44 is configured to pass air but not blood. In such embodiments, blood entering the extravascular system 20 forces air out the vent 44 as it enters the extravascular system 20 and fills it to the vent 44 of the blood sampling device 42. At this point, in some instances, the clamp 38 can close the extension tubing 36 while the blood sampling device 42 is removed and a separate vascular access device, such as an IV line coupled to a fluid reservoir, is coupled to the port 40 to begin an IV therapy process. In other instances, as described below, a clamp 38 is not necessary to prevent blood flow out the port 40.

As described above, the blood sampling device 42 includes a vent 44 that can permit air, but not blood to pass therethrough. The vent 44 can include various materials and components that provide these properties. For example, in some embodiments, the vent 44 includes glass, polyethylene terephthalate (PET), a microfiber material, and/or other synthetic material made of high-density polyethylene fibers, such as TYVEK® material from DuPont. The vent 44 may be hydrophobic or hydrophilic. Other such materials and components can also be used as a layer of the vent or as the entire vent to enable the vent 44 to be hydrophobic and/or air permeable, according to some configurations.

In additional to venting air from the extravascular system 20, the blood sampling device 42 can collect a sample of blood therein that can be used for blood testing or other procedures. Accordingly, in some embodiments, the blood sampling device 42 includes a reservoir (shown in FIG. 2 as 94) therein that can collect blood during the venting process and retain blood after the blood sampling device 42 is removed from the port 40. In some configurations, the reservoir 94 has an internal volume of between about 0.1 mL to about 10 mL. In other configurations, the reservoir 94 has an internal volume of between about 1 mL to about 5 mL. In still other configurations, the reservoir 94 has an internal volume of that is greater than 10 mL. Because different blood tests required different quantities of blood, in some embodiments, the reservoir 94 is sized to retain a quantity of blood needed for a specific blood test or for a specific number of blood tests. In some embodiments, a set of blood sampling devices 42 is provided to a clinician having multiple blood sampling devices 42 of different sizes.

Figure 2:
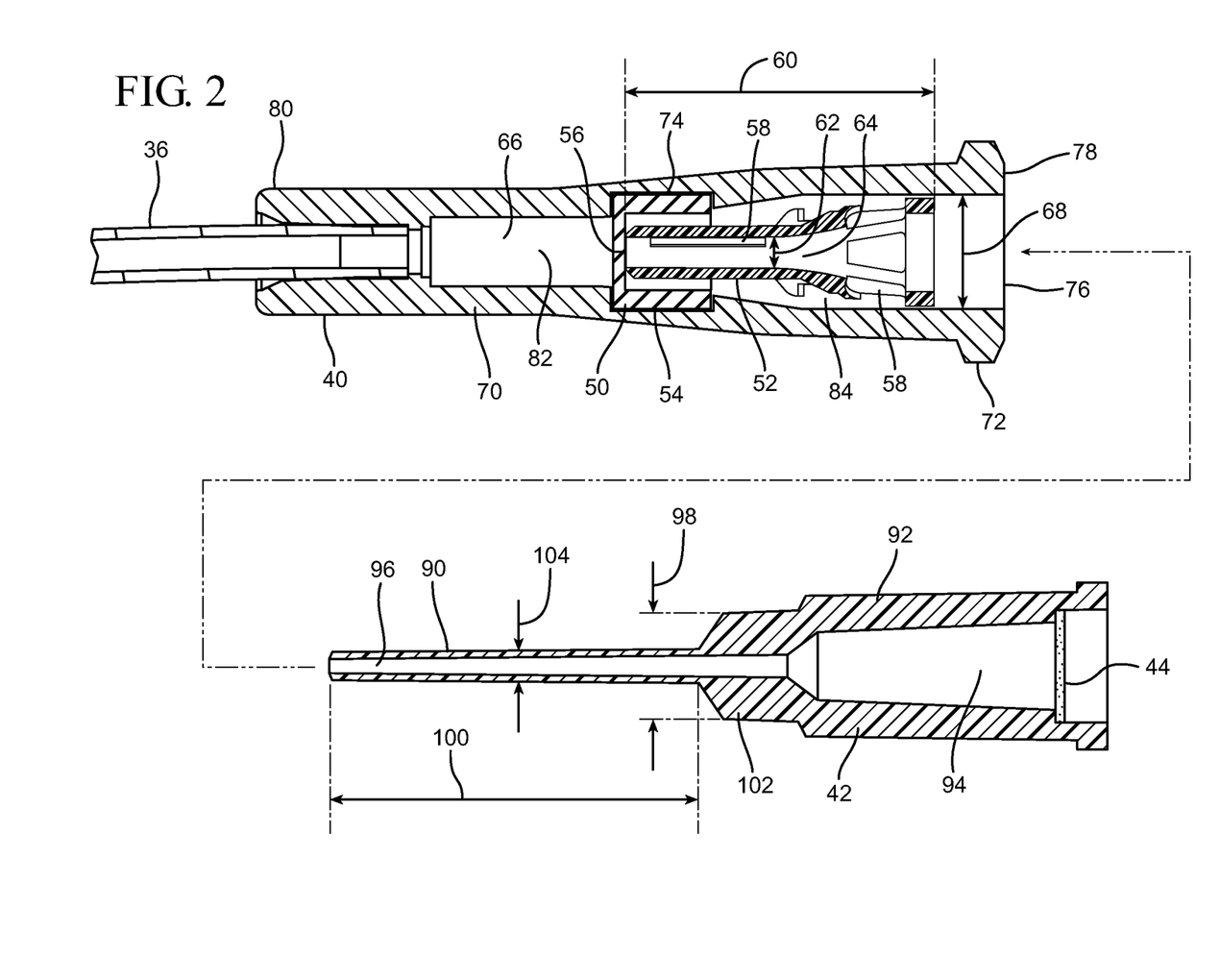
FIG. 2 is a partial cross-sectional view of a port having a blood control valve and a blood sampling device that is separated from the port, according to some embodiments.

Reference will now be made to FIG. 2, which depicts a cross section of a port 40 and a blood sampling device 42, according to some embodiments. As shown, the port 40 comprises a body 70 having lumen 66 extending therethrough. The lumen 66 includes a proximal lumen opening 76 on the proximal end 78 of the body 70 into which a blood sampling device 42 can be inserted. The proximal end 78 of the body 70 can also include one or more Luer threads 72 that can permit a male Luer connector, such as a the male Luer connector 134 of FIG. 7, to connect to the proximal end 78 of the body 70. On the distal end 80 of the body 70 the extension tubing 36 can be connected and aligned in fluid communication with the lumen 66.

Figure 4:
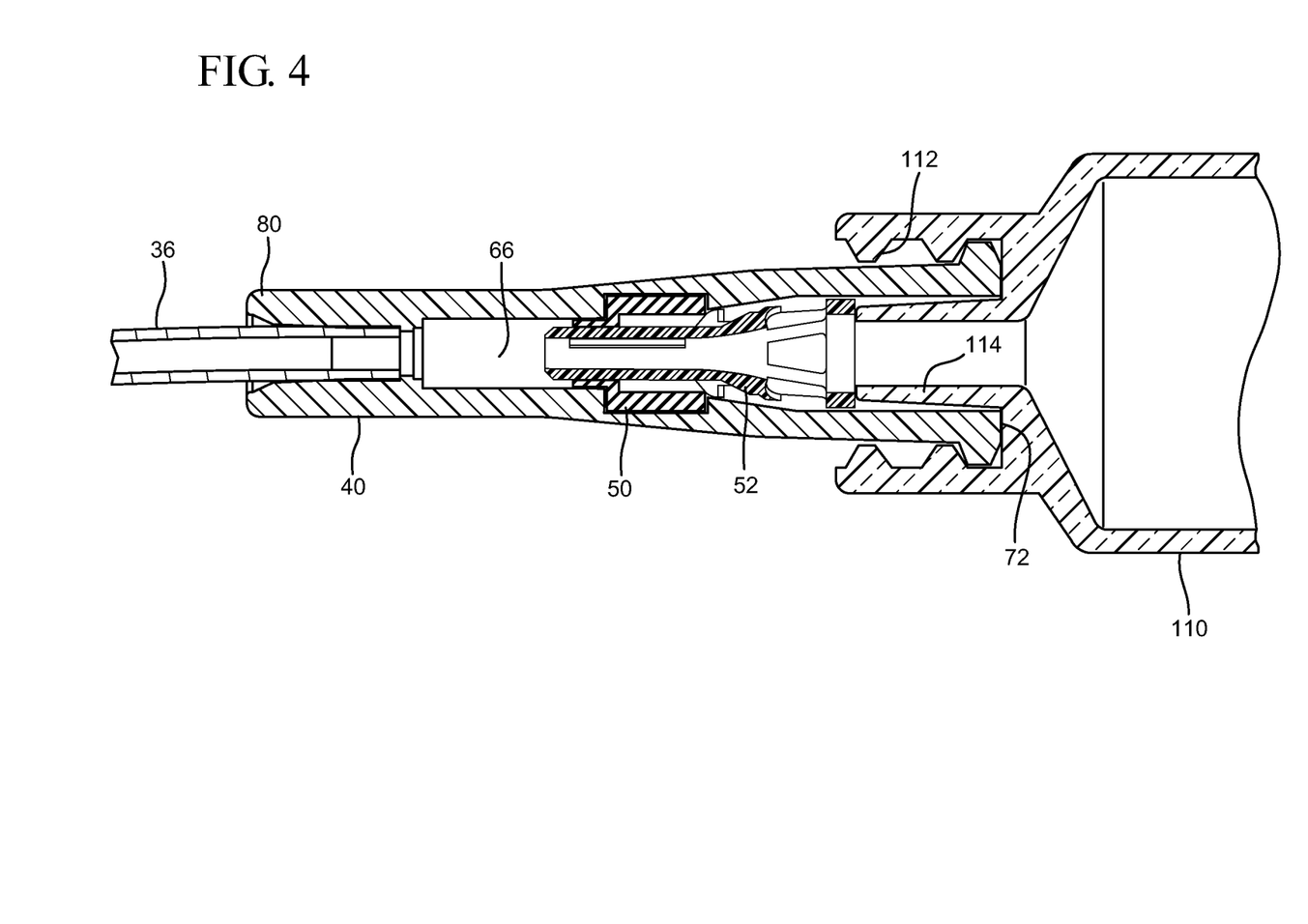
FIG. 4 is a cross sectional view of a port that is accessed by a separate device when the blood sampling device is removed from the port, according to some embodiments.

As shown, in some configurations, the port 40 includes a blood control valve, which is a type of valve that includes a septum 50 and a septum activator 52. The septum activator 52 selectively pierces through the septum 50 to activate, or open, the septum 50. The septum activator 52 is moved distally through the septum 50 when a separate device 110 is inserted through the proximal lumen opening 76 and forces the septum activator 52 distally, as shown in FIG. 4. The process of piercing the septum 50 with the septum activator 52 is partially illustrated in FIG. 5. Once the septum 50 is pierced, fluid can be infused through the septum 50. Non-limiting examples of ports 40 having a blood control valve therein are described in United patent application Ser. No. 13/042,103 filed Mar. 7, 2011, entitled SYSTEM AND METHOD FOR PROVIDING A FLUSHABLE CATHETER ASSEMBLY, (herein the "Flushable Catheter Assembly reference") which is incorporated herein by reference in its entirety. In some configurations, the port 40 can have any of the various configurations of blood control valves described in the Flushable Catheter Assembly reference. The Flushable Catheter Assembly reference and the patents to which it claims priority (which are also herein incorporated by reference in their entirety, and referred to as the "Parent Reference") depend also describes the use of a blood control valve in a catheter assembly 24. While the use of a blood sampling device 42 is generally described herein as being used with a port 40 having a blood control valve within an inner lumen 66 of the body 70 of the port 40, it will be understood that the blood sampling device 42 can, in some configurations, additionally or alternatively be used with a catheter assembly 24 having a blood control valve within the inner lumen of the body of the catheter assembly 24. Accordingly, in some configurations, the various embodiments of a blood sampling device 42 as described herein can be used with any of the various configurations of blood control valves in a catheter assembly described in the Flushable Catheter Assembly reference and the Parent References.

As shown in FIG. 2, in some configurations, the blood control valve of the port 40 includes a septum 50 disposed within a groove 74 in the inner lumen 66 of the body 70. In some instances, one or more ventilation channels are disposed between the septum 50 and the body 70 to provide a channel for air to be vented around the septum 50, as described in the Flushable Catheter Assembly reference. The one or more channel can be used to vent air from an extravascular system 20. In other instances, there are no ventilation channels between the septum 50 and the body 70, but an air tight connection is formed at this interface 54. The lack of ventilation channels can prevent air or blood from flowing around the septum 50. In such instances, air can be vented from the extravascular system 20 through the vent 44 of the blood sampling device 42.

In some configurations, the septum 50 can also serve to divide the inner lumen 66 into a distal chamber 82 and a proximal chamber 84 and provide a seal between these two chambers. A septum activator 52 can be disposed in the proximal chamber 84. In some embodiments, the septum activator 52 has an inner passage 64 extending therethrough. The septum activator 52 can have one or more flow diversion channels 58 formed through it that permit fluid flow between the areas outside the septum activator 52 into the inner passage 64 to provide flushability within the inner lumen 66 and within the septum activator 52.

FIG. 2 further depicts a blood sampling device 42 that can be inserted into the port 40 to vent air from the extravascular system 20 while bypassing function of the septum activator 52. In some configurations, a tube 90 of the blood sampling device 42 extends out from its body 92 a long enough distance to pass entirely through and bypass the septum activator 52 when the blood sampling device 42 is connected to the port 40. Thus, in some instances, the length 100 of the tube 90 is greater than the length 60 of the septum activator 52. Additionally, in some instances, a width 104 of the tube 90 is less than an inner width 62 of the inner passage 64 of the septum activator 52. Thus, the dimensions of this tube 90 can permit it to be inserted through the inner passage 64 of the septum activator 52 and pierce through the septum 50 without lodging within and advancing the septum activator 52 forward. Accordingly, in some configurations, the outer geometry of the tube 90 approximate or is smaller than the inner geometry of the inner passage 64 when the tube 90 is fully inserted through the inner passage 64. Thus, for example, if the inner passage 64 tapers from a larger diameter to a smaller diameter, the outer geometry of the tube 90 can likewise taper from a larger diameter to a smaller diameter or otherwise be smaller than the geometry of the inner passage 64. Accordingly, the outer geometry of the tube 90 can be shaped and sized into various configurations, to fit within the inner passage 64 of the septum activator 52 when the tube 90 is fully inserted through the inner passage 64.

Figure 3:
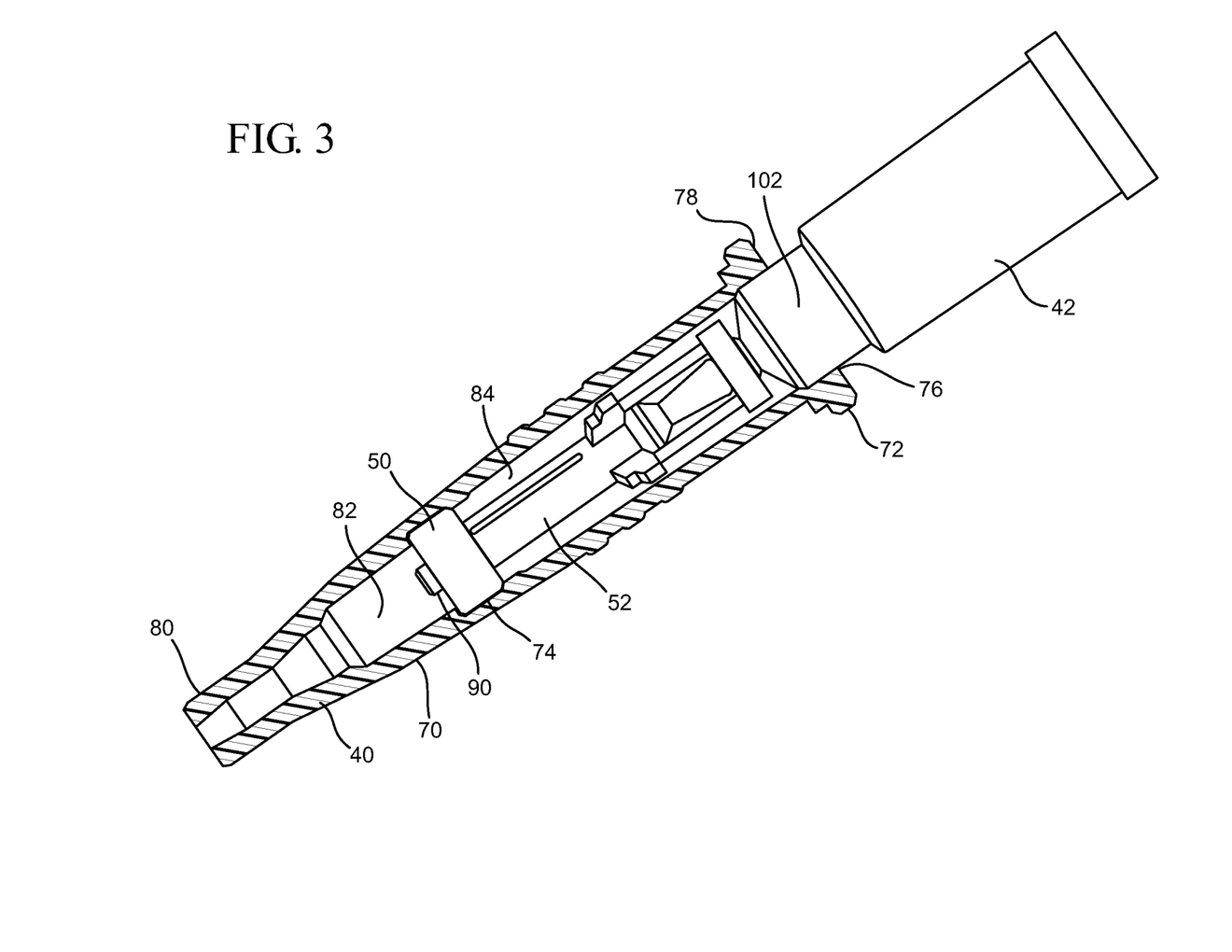
FIG. 3 is a partial cross-sectional view of a blood sampling device that has been inserted into the port, according to some embodiments.
Figure 7:
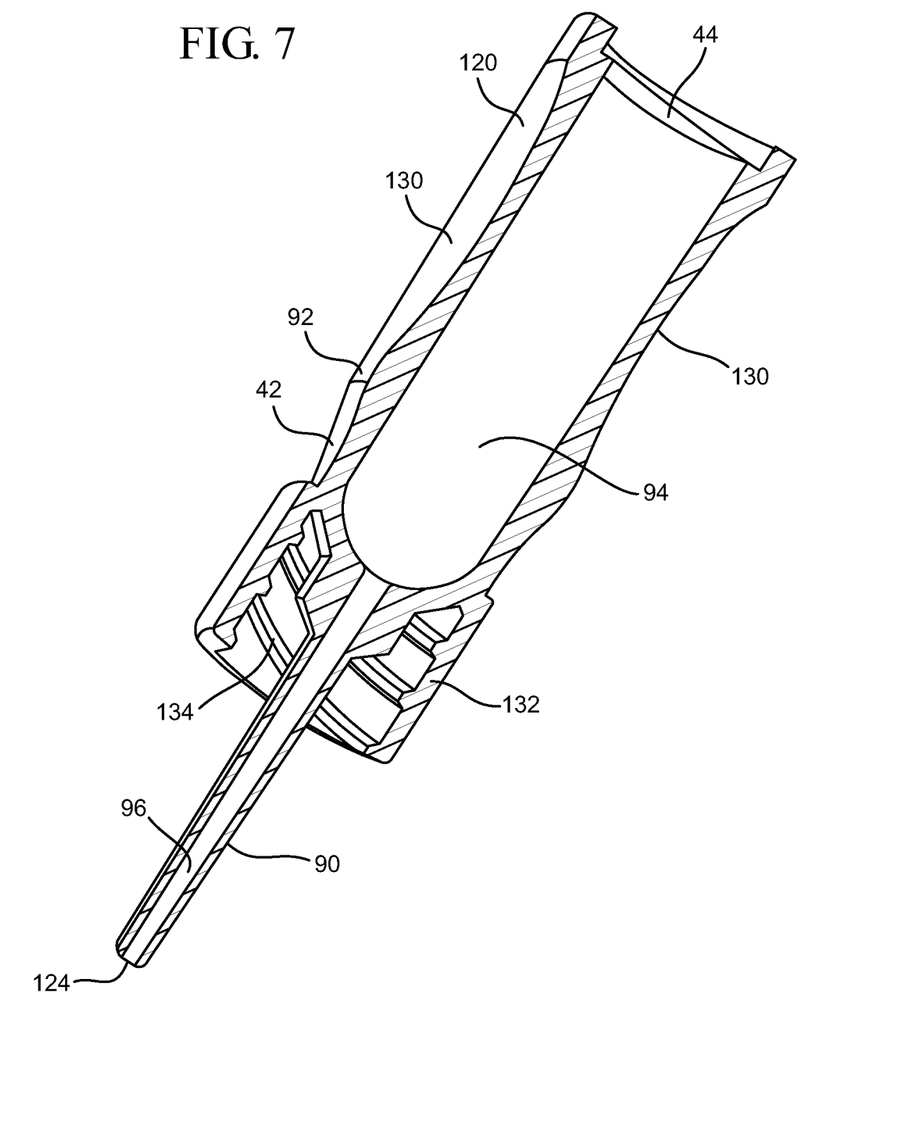
FIG. 7 is a perspective view of another blood sampling device, according to some embodiments.

Reference will now be made to FIGS. 2 and 3, in some embodiments, the blood sampling device 42 can be press fit into the proximal lumen opening 76 of the inner lumen 66 of the port 40. This connection can prevent air and blood from leaking out the port 40. This connection is formed between a distal portion 102 of the body 92 of the blood sampling device 42 and the proximal portion of the inner lumen 66 of the port 40. In some configurations, the outer geometry of the distal portion 102 approximates the inner geometry of the proximal portion of the inner lumen 66. In some configurations, these geometries are substantially circular and the outer diameter 98 of the distal portion 102 is approximately equal to the inner diameter 68 of the proximal portion of the inner lumen 66. In these and other configurations, the blood sampling device 42 can be press fit into the proximal lumen opening 76 of the port 40. In other configurations, as shown in FIG. 7, the blood sampling device 42 connects to the port 40 via a threaded Luer connection rather than a press fit connection. Likewise, other types of connections can be incorporated between the blood sampling device 42 and the port 40.

With continuing reference to FIGS. 2 and 3, the blood sampling device 42 has a body 92 that defines a reservoir 94 therein that can be used for collecting and retaining a sample of blood. When the blood sampling device 42 is fully inserted into the port 40, the distal tip of the tube 90 extends through the one or more slits 56 in the septum 50. By thus breaching the septum 50, an air path is created through the interior 96 of the tube 90, through the reservoir 94, and out the vent 44. Vent 44 can be in fluid communication with the reservoir 94 so that air can flow into the reservoir 94 and out the vent 44. This air path can permit air to be vented from the extravascular system 20. In some configurations, the septum 50 can contact the outer surface of the tube 90 and prevent or substantially prevent air and blood from flowing between the tube 90 and the septum 50.

As described above, as air is vented from the extravascular system 20, blood flows into the system and fills or substantially fills the reservoir 94. After a clinician recognizes that the extravascular system 20 is vented and the reservoir 94 has collected a sample of blood, the clinician can remove the blood sampling device 42. As the tube 90 of the blood sampling device 42 is withdrawn proximally through the septum 50, the one or more slits 56 of the septum 50 close sealing the proximal chamber 84 from the distal chamber 82 and the blood contained therein. As mentioned above, in some instances, a clamp 38 is not necessary since the blood control valve can automatically seals the port 40 before and after the blood sampling device 42 is inserted into the port 40.

Referring now to FIG. 4, after the blood sampling device 42 is removed from the port 40 a separate device 110 can be coupled to the port 40 to infuse a fluid through the port 40 into the extravascular system 20. In some instances, the separate device 110 is vascular access device, such as an intravenous fluid line. In some configurations, the separate device 110 includes a male Luer connector 134 that connects to the female Luer threads 72 of the port 40. As shown, as the separate device 110 is inserted into the port 40, a probe member 114 of the separate device 110 contacts the septum activator 52, forcing it forward through the septum 50, opening the septum 50. With the septum 50 opened, fluid can be infused through the port 40 into the extravascular system 20.

Figure 5:
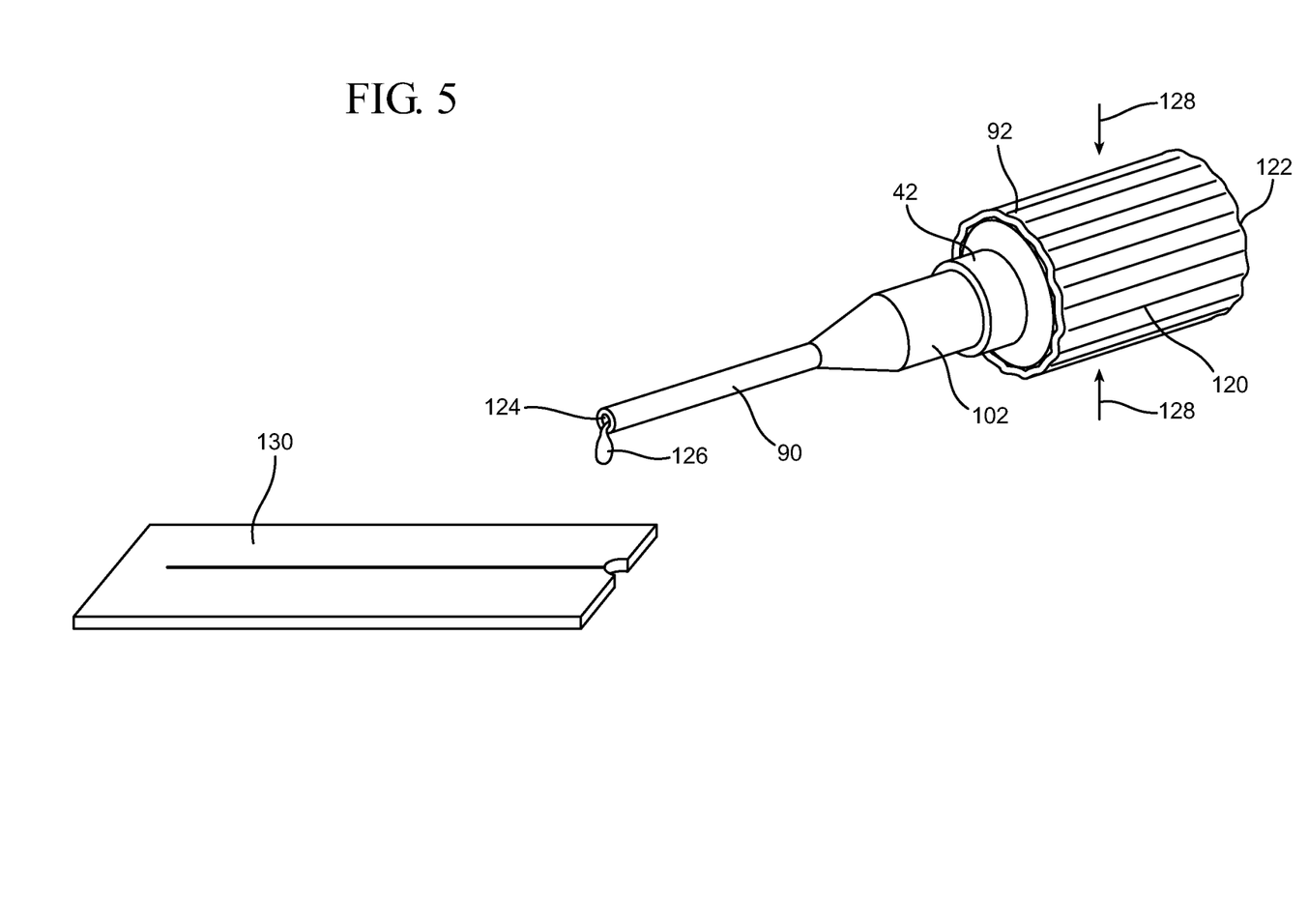
FIG. 5 is a perspective view of a blood sampling device being compressed and blood dripping onto a blood test strip, according to some embodiments.

Referring now to FIG. 5, after the blood sampling device 42 is removed from the port 40, the collected blood 126 can be used for analysis and testing. Accordingly, in some configurations, the blood sampling device 42 is configured to eject at least a portion of the blood 126 from the reservoir 94. For example, in some embodiments, the blood sampling device 42 has a body 92 with a compressible portion 120. A compressible portion 120 can include any means to reduce the size of the reservoir volume in order to eject a sample of fluid within the reservoir 94. For example, the compressible portion 120 can comprise the entire body 92 being flexible or semi-flexible. Or the compressible portion 120 may be limited to a limited portion of the body 92, which flexes. In a non-limiting example, a compressible portion 120 is disposed between two or more rigid portions, such that the compressible portion 120 compress when the more rigid portions are pressed inwardly 128. In some embodiments, to facilitate compression and gripping, the body 92 includes ridges or other gripping member 122.

In some embodiments, the blood sampling device 42 is configured to eject blood 126 when compressed and retain blood 62 when it is not compressed. As such, as the blood sampling device 42 is withdrawn from the port 40 it retains blood therein (unless it is compressed), which prevents blood exposure to the clinician removing the blood sampling device 42. Thus, in some configurations, the inner dimensions of the tube 90 and/or the dimension so the tube opening 124 is shaped and sized to retain blood 126. Blood retention within the tube 90 is governed, at least in part, by the inner perimeter of the tube 90, the surface tension of blood, and the force on the blood 126 to flow out of the distal tube opening 124. Accordingly, the inner perimeter of the tube 90 can be designed so that blood 126 is retained within the reservoir 94 when the force of the blood 126 to flow out of the distal tube opening 124 is within a certain range, but permit at least some blood to flow out when the pressure on the blood 126 exceeds this range.

For example, in some instances, the inner dimensions of the tube 90 are substantially circular and the inner perimeter is less than or equal to approximately 2.0 mm with a diameter 60 of less than or equal to approximately 0.6 mm. In these instances, the tube 90 permits the retention of blood against approximately the force of gravity. When the force on the blood 126 is greater than the force of gravity some blood 126 can flow out of the distal tube opening 124. In other instances, a circular distal tube opening 124 with a diameter of about 0.3 mm can retain blood 126 therein against forces stronger than gravity, such as bumping, jarring, and movement of the filled blood sampling device 42. When the distal tube opening 124 has a very small inner perimeter, the force required to expel blood 126 can be very large.

Thus, in some embodiments, the inner perimeter of the tube 90 has a inner perimeter greater than or equal to about 0.3 mm, which when the inner perimeter of the tube 90 is a circular opening, corresponds to a diameter of about 0.1 mm. Thus, in some configurations, the inner perimeter of the tube 90 has an inner perimeter between about 0.3 mm to about 2.0 mm. In some configurations, the inner perimeter of the tube 90 is approximately circular and has a diameter between about 0.1 mm to about 0.6 mm. In other embodiments, the inner perimeter of the tube 90 is non-circular.

To eject blood 126 from the blood sampling device 42, the compressible portion 120 or compressible portions 120 can be compressed. This compression decrease the volume increases the internal pressure of the reservoir 94. As the internal pressure increases it becomes larger than the forces preventing the blood 126 from flowing out of the tube 90, thus causing blood 126 to flood out of the tube 90. The amount of blood 126 that is ejected from the distal tube opening 124 can depend on the amount of force applied to the compressible portion 120. The blood 126 can be ejected onto a blood test strip 130, into a diagnostic cartridge, or onto another type of blood testing/analysis device.

Figure 6:
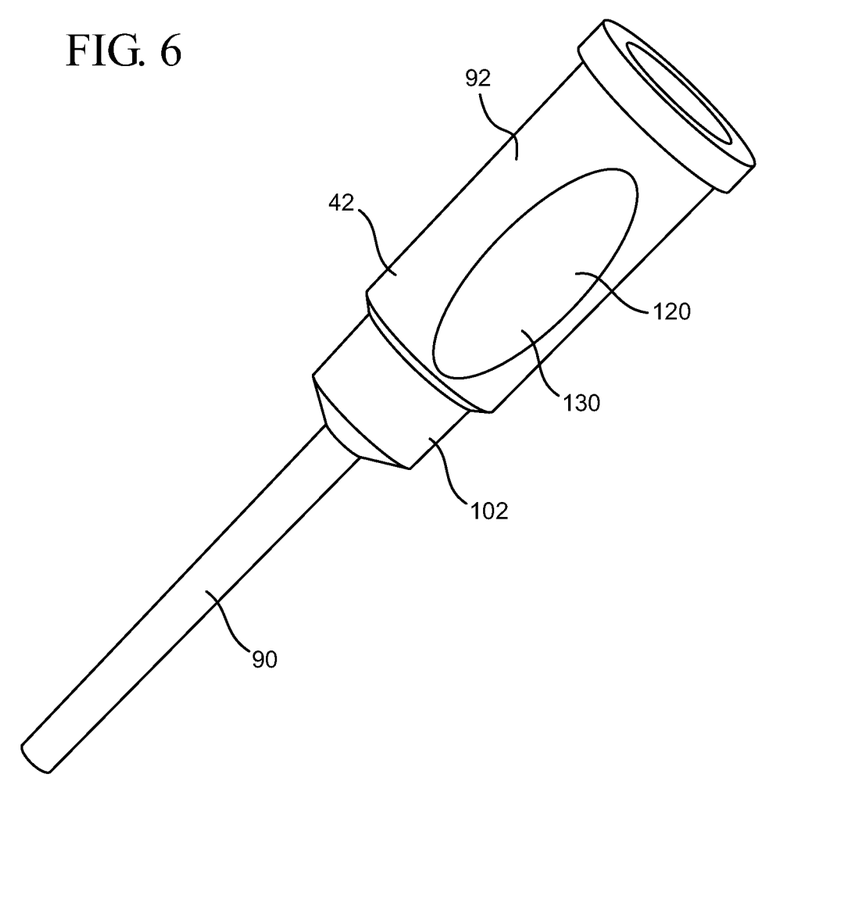
FIG. 6 is a perspective view of a blood sampling device, according to some embodiments.

FIGS. 6 and 7 will now be discussed. These figures depict specific embodiments of a blood sampling device 42. FIG. 6 depicts a blood sampling device 42, similar to that of FIGS. 2 and 3 that can be press fit into the proximal lumen opening 76 of a port 40. As shown, the body 92 includes one or more compressible portions 120 and a grip indent 130. The grip indent 130 provides a visual and tactile indication of where a finger can be placed to effectively grip and compress the compressible portion 120. In some instances, another grip indent 130 is disposed on the opposite side of the body 92.

FIG. 7 depicts a blood sampling device 42 that can be interlocked with the Luer threads 72 of a port 40. In some configurations, as shown, the body 92 includes an alternative distal body portion 132 that comprises a threaded male Luer connector 134. This threaded male Luer connector 134 can interconnect with the female Luer connector 72 of the port 40 to interlock the blood sampling device 42 thereto. This interconnection can provide additional strength and stability over other types of connections.

From the foregoing, it will be seen that these systems and methods are developed to provide a blood sampling device 42 that can vent air from an extravascular system 20 and simultaneously collecting a sample of blood 126. In some embodiments, a blood sampling device 42 replaces prior devices and procedures that took more time, used more parts, and cost more than the present blood sampling device. The blood sampling device 42 can be inserted into a port 40, left there while it automatically vents air from the extravascular system 20, then withdrawn with a sample of blood 126 automatically collected within its internal reservoir 94.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An extravascular system comprising:
a body having a proximal end, a distal end, and an inner lumen extending therethrough;
a septum disposed within the inner lumen and dividing the inner lumen into a distal chamber and a proximal chamber;
a septum activator disposed within the proximal chamber of the inner lumen proximal the septum, the septum activator having an inner passage extending therethrough; and
a blood sampling device separate and apart from the septum activator, and having a distal portion that couples to the proximal end of the body when the blood sampling device is inserted into the body, the blood sampling device having a tube extending outwardly from the distal portion and comprising a tip that passes through the septum activator and the septum and remains is positioned within the distal chamber when the blood sampling device is inserted into the body such that the tube passes through the septum without causing the septum activator to pass through the septum, the tube having an interior in fluid communication with the tip and a reservoir of the blood sampling device, the blood sampling device further comprising a vent in fluid communication with the reservoir and being capable of passing air but not blood therethrough.

2. The extravascular system of claim 1, wherein an outer diameter of the tube is less than an inner diameter of the inner passage of the septum activator.

3. The extravascular system of claim 1, wherein the septum divides and substantially seals the distal chamber of the inner lumen from and the proximal chamber of the inner lumen, the septum having one or more slits therein, the septum activator being movable from an un-activated position in the proximal chamber to an activated position that extends through the slit of the septum into the distal chamber.

4. The extravascular system of claim 1, wherein the blood sampling device has a portion of an outer geometry approximately equal to that of the inner lumen of the body such that the blood sampling device can be press fit within the inner lumen of the body.

5. The extravascular system of claim 1, wherein the blood sampling device has a Luer connector that selectively interlocks with a Luer connector disposed on the body.

6. The extravascular system of claim 1, wherein the body is either a catheter assembly or a Luer access port.

7. The extravascular system of claim 1, wherein the septum and the body form a fluid tight connection that circumscribes the septum.

8. The extravascular system of claim 1, wherein the reservoir has a volume equal to or greater than about 0.1 mL.

9. The extravascular system of claim 1, wherein the tube has a length greater than or equal to about 5 mm and a width of less than or equal to about 3 mm.

10. The extravascular system of claim 1, wherein at least a portion of the blood sampling device defining the reservoir is compressible and decreases the internal volume of the reservoir when compressed.

11. An extravascular system comprising:
a body having an inner lumen;
a septum disposed within the inner lumen and separating the inner lumen into a proximal chamber and a distal chamber;
a septum activator disposed within the inner lumen proximal the septum, the septum activator having an inner passage extending therethrough; and
a blood sampling device comprising a tube having a tip that extends through the inner passage of the septum activator and through an opening in the septum to a maximum insertion depth that locates the tip within the distal chamber of the inner lumen without causing the septum activator to pass through the septum such that the septum activator remains proximal to the septum when the tip is positioned distal to the septum, the blood sampling device having a reservoir in fluid communication with the tube and the tip, and further comprising a vent in fluid communication with the reservoir, the vent passing air but not blood therethrough.

12. The extravascular system of claim 11, wherein the septum divides and substantially seals the distal chamber of the inner lumen from and the proximal chamber of the inner lumen, the septum having one or more slits therein, the septum activator being movable from a un-activated position in the proximal chamber to an activated position that extends through the slit of the septum into the distal chamber.

13. The extravascular system of claim 11, further comprising a removable seal disposed across the vent preventing air from passing through the vent.

14. The extravascular system of claim 11, wherein the blood sampling device is removably coupled to the body.

15. The extravascular system of claim 11, wherein the septum and the body form a fluid tight connection that circumscribes the septum.

\* \* \* \* \*